United States Patent [19]

Morii et al.

[11] Patent Number: 4,898,825
[45] Date of Patent: Feb. 6, 1990

[54] METHODS FOR PURIFICATION OF SINGLE-CHAIN AND DOUBLE-CHAIN TISSUE PLASMINOGEN ACTIVATOR

[75] Inventors: Mitsuyoshi Morii; Masaharu Ohoka, both of Yokohama; Toshihiko Suzuki, Tokyo; Katsuyuki Suzuki, Hiroshima; Nobuhiro Kawashima, Sagamihara; Noriko Morii; Kunizo Mori, both of Yokohama, all of Japan

[73] Assignee: Mitsui Toatsu Chemicals, Incorporated, Tokyo, Japan

[21] Appl. No.: 43,746

[22] Filed: Apr. 29, 1987

[30] Foreign Application Priority Data

May 7, 1986 [JP] Japan ................................. 61-103200
Aug. 11, 1986 [JP] Japan ................................. 61-186850

[51] Int. Cl.4 ........................... C12N 9/48; C12N 9/64
[52] U.S. Cl. .................................... 435/212; 435/226; 435/814; 435/815
[58] Field of Search ............... 435/212, 215, 219, 226, 435/183, 815, 814

[56] References Cited

U.S. PATENT DOCUMENTS 4,766,075  8/1988  Goeddel et al. .................. 935/70 X

FOREIGN PATENT DOCUMENTS 0112122  6/1984  European Pat. Off. ............ 435/226
87/01389  3/1987  World Int. Prop. O. .......... 435/212

Primary Examiner—Jayme A. Huleatt
Attorney, Agent, or Firm—Nixon & Vanderhye

[57] ABSTRACT

A mixture containing a single-chain tissue plasminogen activator (tPA) and/or double-chain tPA is brought into close contact with a column carrying an immobilized *Erythrina trypsin* inhibitor as an affinity agent. Adsorbed protiens are eluted with eluents having different pHs with or without arginine or benzamidine, so that single-chain tPA is obtained in the eluent with a pH at least 4.5 and double-chain tPA is obtained in the eluent with a pH lower than 4.5.

18 Claims, No Drawings

METHODS FOR PURIFICATION OF SINGLE-CHAIN AND DOUBLE-CHAIN TISSUE PLASMINOGEN ACTIVATOR

BACKGROUND OF THE INVENTION (1) Field of the Invention

This invention relates to a method for purifying single-chain and/or double-chain tissue plasminogen activator (hereinafter referred to as sc-TPA and dc-TPA, respectively) from a mixture containing sc-TPA and/or dc-TPA.

(2) Description of the Prior Art tPA (tissue plasminogen activator) is a protein which is produced in a tissue of a higher animal, serves to activate plasminogen, a precursor of plasmin which is known to be a proteolytic enzyme specifically to fibrin, and has now being brought into a focus as a potential thrombolytic agent.

tPA has two molecular forms, single-chain tPA and double-chain tPA, having the same molecular weight (about 70,000 daltons) and is obtained as a mixture in ordinary procedures for tPA production. A double-chain form has about 10-fold higher activity for activation of plasminogen than a single-chain form (European Patent Publication No. 112122A). However, it is known that sc-TPA has a stronger capacity of binding to fibrin than dc-TPA and, once bound to fibrin, quickly converted to dc-TPA (D. C. Rijken et al., J. Biol. Chem. 257, 2920–2925, 1982). Consequently, in order to realize an effective treatment of thrombosis by tPA, an increased binding capacity of tPA to fibrin in the clotting of blood must be obtained by using a tPA mixture containing an increased amount of sc-TPA or by using a preparation containing sc-TPA only.

Under these circumstances and also in order to investigate properties and functions of tPA in more detail, there has been a great need for improving methods for obtaining single-chain form exclusively and for isolating single-chain and double-chain form separately from a mixture thereof.

A method previously known for preparing tPA, for example, comprises culturing cells, which are indigenously capable of producing tPA or manipulated to carry the tPA gene, and then isolating tPA from the resultant cultured cells and/or from the culture supernatant. For example, the above-mentioned European Patent Publication No. 112122A disclosed a method of purifying tPA using an Erythrina trypsin inhibitor (hereinafter referred to as ETI), or an immobilized Kunits inhibitor, which is produced in seeds of *Erythrina latissima* and other Erythrina plants and acts as an inhibitor to trypsin, plasmin and tPA but not to urokinase. In this method, however, a separate isolation of sc-TPA from dc-TPA was not taken into consideration.

In a method previously known for preparing sc-TPA, a proteinase inhibitor such as Aprotinin is added to a culture medium to suppress conversion of tPA from single-chain to double-chain form (D. C. Rijken et al., J. Biol. Chem. 256, 7035–7041, 1981).

In another method for purifying sc-TPA, an immobilized monoclonal antibody which adsorbs specifically sc-TPA is used (catalogue by BioPool, Sweden). This method, however, is inferior to the method with ETI in respect to the capacity of adsorbing tPA and stability of a column to be used. Moreover and disadvantageously, this method can not remove an impurity which is a protein with a molecular weight of 110,000±20,000 daltons and potentially acts as an antigen to react with an anti-human tPA antibody.

SUMMARY OF THE INVENTION

In the course of various investigations on methods for purifying tPA from a crude tPA preparation in tPA production, four of the present inventors applied for a patent for the invention which comprises a method for isolating and removing a protein which has a molecular weight of 110,000±20,000 daltons and reacts with an anti-human tPA antibody produced in a culture medium containing fetal calf serum; and a method for culturing transformed cells produced by gene manipulation and separating selectively human-cell derived tPA from host-cell derived tPA (U.S. patent application Ser. No. 887,514).

And further, in the course of extensive investigations on various characteristics of sc-TPA and dc-TPA, the present inventors found out that these two forms of tPA vary in an affinity with the ETI and have now completed the present invention as a result of this finding.

An object of the present invention is to provide a method for isolating sc-TPA and dc-TPA effectively and easily from a mixture thereof.

Another object of the present invention is to provide a method for isolating sc-TPA and/or dc-TPA from a crude tPA preparation which contains sc-TPA and/or dc-TPA.

Methods to accomplish these objects comprise the steps of bringing a mixture containing sc-TPA and/or dc-TPA into close contact with an immobilized ETI column to adsorb tPA and then eluting selectively desired sc-TPA and/or dc-TPA by changing the pH of eluents to elute tPA.

In one aspect of this invention, one of the two forms exclusively or two forms can be isolated from each other and purified as desired.

In another aspect of this invention, sc-TPA and/or dc-TPA can be more effectively isolated and purified by adding guanidine or amidine derivative, such as arginine or benzamidine, to eluent to elute tPA from a column.

The present invention is applicable independently of a type of cells to produce tPA. More precisely, sc-TPA and/or dc-TPA can be isolated from any of mammalian cells such as melanoma cells and human normal cells or from cells with incorporated human tPA gene by gene manipulation. In addition, the present invention makes it possible to isolate and purify sc-TPA and dc-TPA from a serum-added medium the same as from a serum-free medium, that is, independently of a constituent of a culture medium.

DETAILED DESCRIPTION OF THE PREFERRED EMBODIMENTS

In one aspect of the present invention, a mixture containing sc-TPA and dc-TPA is first run through a column carrying an immobilized ETI to adsorb tPA, sc-TPA is then eluted with an eluate having a pH at least 4.5 and dc-TPA is eluted with an eluate with a pH lower than 4.5.

In another aspect of the present invention, a mixture containing sc-TPA and/or dc-TPA is run through a column carrying an immobilized ETI, and then if sc-TPA only is desired, the column is treated with an eluent with a pH at least 4.5 and if dc-TPA only is desired, the column is treated with an eluent with a pH lower than 4.5. Thus, either of sc-TPA or dc-TPA can be isolated and purified as needed.

In another aspect of the present invention, the above-mentioned procedure for isolation and purification can be more efficiently carried out by adding an amidine derivative or a guanidine derivative, such as arginine and benzamidine, as an additive to the eluent. For example, an eluting pattern with sufficiently sharp activity peak(s) for tPA can be always obtained under various eluting conditions which include varieties in a column size and the like.

Preferred examples of a carrier for ETI immobilization in the present invention include insoluble agarose, dextran, cellulose, polyacrylamide, and polyethylene glycidylmetacrylate polymer. Preferred examples of a method for ETI immobilization include conventionally known methods such as, typically, a method of binding ETI to a carrier being pre-activated with cyanogenbromide, a carbo-imido coupling method in which a free amino group is bound to a free carboxyl group, and a glutar-aldehyde coupling method in which an amino group is bound to a carrier previously converted to an aminoalkyl form. Another example of an immobilized ETI carrier is a periodate-activated one, in which an aldehyde group formed therein reacts with an amino group in ETI at a pH between 4 to 6 to form a Schiff base, and is then reduced by sodium borohydride or sodium cyanoborohydride. Further, a material for a carrier can be converted to a hydrazid-succinyl derivative in which a carboxyl ligand is to be bound to an amino group through EDC (1-ethyl-3-(3-dimethylaminopropyl)carbodiimide) or diazonization. Cellulose fibers and particles are to be converted to a hydrazid derivatives and can be applied according to the method of Parikh et al (Methods in Enzymology, 34, 77–102, editors; W. B. Jakobi and Wilcheck, Academic Press, N.Y.). Polyacrylamide particles can be bound directly by a glutar-aldehyde coupling method or through diazonization of a p-aminobenz-amidoethyl derivative or a hydrazid derivative.

Eluents to be used for eluting tPA according to the present invention include acid solutions having pHs below 6, water-soluble salt solutions and buffer solutions.

Preferred examples of such an acid solution include that containing at least one acid selected from the group of acids comprising, typically, citric acid, oxalic acid, lactic acid, succinic acid, acetic acid, phthalic acid, glutamic acid, aspartic acid, adipic acid, phosphoric acid, and hydrochloric acid.

Preferred examples of such a water-soluble salt solution include aqueous solutions containing at least one salt selected from the group of salts comprising, typically, sodium chloride, potassium chloride, lithium chloride, ammonium chloride, barium chloride, calcium chloride, magnesium chloride, sodium sulfate, ammonium sulfate, potassium nitrate, potassium thiocyanate, and sodium thiocyanate, ammonium thiocyanate.

Further, preferred examples of such a buffer solution include a sodium phosphate buffer, a potassium phosphate buffer, a Veronal buffer, admixtures in a combination such as sodium phosphate-phosphoric acid, potassium phosphate-phosphoric acid, citric acid-sodium citrate, succinic acid-borate, lactic acid-sodium lactate, acetic acid-sodium acetate, oxalic acid-sodium oxalate, glycine-hydrochloric acid, and potassium hydrogenphthalate-sodium hydroxide.

These eluents may further contain one or more water soluble organic solvents.

Preferred concentrations of an additive consisting of an amidine derivative or a guanidine derivative to be used for eluting tPA range from 1 mM to the maximum solubility thereof. For example, at a pH between 4.5 to 6.0, a concentration applicable decreases in proportion to an approach of the pH to 4.5, while a higher concentration is needed in proportion to an approach of the pH to 6.0.

An embodiment of the present invention comprises running a cell culture supernatant containing human tPA through an ETI column to adsorb tPA, removing undesired proteins by washing, subsequently recovering from the column sc-TPA using an eluent with a pH ranging from 4.5 to 6.0 with an additive and then recovering dc-TPA by changing the pH of an eluent below 4.5.

It is known to those skilled in the art that an amidine derivative or a guanidine derivative binds competitively to an active center of a trypsin-like proteinase to dissociate an enzyme-inhibitor complex. However, it is entirely a novel technique to apply this phenomena in such a specific mean as isolation of sc-TPA and dc-TPA in most appropriate conditions for the isolation.

If a starting material to be treated according to the present invention possibly contains a small quantity of undesired substances such as trypsin-like enzymes, etc., these substances may be adsorbed to or desorbed from ETI and act as interfering factors in the purification process according to the present invention. Consequently, if necessary, a pre-treatment for removing these undesired substances is to be recommended.

This removing procedure is carried out by using an immobilized soybean trypsin inhibitor (hereinafter referred to as STI), or another Kunits-type inhibitor, which is produced in soybean seeds and has a similar molecular weight to ETI and an amino acid sequence homologues to ETI by 80% or more.

STI is very similar to ETI in its specificity, but does not inhibit tPA. A combined use of these two inhibitors results in a selectivity comparable to that accomplished by using an immobilized anti-human tPA monoclonal antibody. This procedure comprises running a cell culture supernatant containing human tPA through an immobilized STI column to bind for removal a portion of a small quantity of undesired proteinases included in the culture supernatant, then running a resultant affluent through an immobilized ETI column to bind tPA, washing the ETI column to remove undesired proteins, and finally isolating and purifying sc-TPA and dc-TPA separately by changing pHs of eluates.

In an accordance with an important aspect of the present invention, there is provided a method which is applicable independently to the type of cells containing tPA. To be more precise, the present invention makes it possible to isolate and purify sc-TPA and/or dc-TPA from any type of cells such as melanoma cells, human normal cells and cells transformed with human tPA gene by gene manipulation. In addition, the present invention also makes it possible to isolate and purify sc-TPA and/or dc-TPA from a serum-added culture supernatant the same as from a serum-free culture supernatant, that is, independently of a constituent of culture medium.

In accordance with another outstanding aspect of the present invention, the method provided is appropriately applicable at any desired stages of isolation and purification of sc-TPA and/or dc-TPA in various treatments of, or preparative procedure for, tPA. For example, isolation and purification of desired sc-TPA and/or dc-TPA is accomplished by culturing cells capable of producing tPA to produce tPA and then treating a resultant mixture derived from the culture by the method according to the present invention. A mixture derived from the culture means a crude extract of culture cells, a cell-free culture supernatant or a processed material of these. Any of these is chosen as needed.

Other important aspects of the present invention will be understood from the following description of embodiments for the purification of human tPA.

EXAMPLE 1

A column carrying an immobilized affinity agent, ETI or STI, to be used in the examples hereinafter was prepared in the following manner.

In accordance with the method of Joubert et al. (Hoppe-Seyler's Z. Physiol. Chem. 362, 531–538, 1981), seeds of *Erythrina latissima* were collected and prepared. Ground and defatted seeds were allowed to stand overnight at 10° C. in a 0.5M NaCl solution for extraction. The solution with the seeds were centrifuged to collect supernatant and the intended substance was collected from the supernatant by ammonium sulfate precipitation. The material thus prepared was subjected to chromatography successively on Sephadex G-50 (Pharmacia Fine Chemicals), DEAE-cellulose (Phoenix Chemicals) and DEAE-Sepharose (Pharmacia Fine Chemicals). The resultant purified preparation, exhibited a single band of an apparent molecular weight of 22,000 daltons when subjected to electrophoresis in a 15%-polyacrylamide gel containing 0.1% sodium dodecylsulfate (SDS).

Twenty six milligrams of this purified preparation was to be bound onto 5 ml of bromocyanide-activated agarose (Sepharose, Pharmacia Fine Chemicals), equilibrated with a phosphate buffer, pH 7.4, containing 0.4M NaCl, 0.1% Triton X-100 (Wako Jun-yaku Co., Japan) and 0.02% sodium azide as an stabilizer, and was finally packed into a disposable plastic syringe to form a 5-ml column (hereinafter referred to as ETI-Sepharose column).

Twenty five milligrams of Chromatographic pure STI (from Sigma Co.) was bound to 5 ml of bromocyanide-activated agarose, equilibrated with a phosphate buffer, pH 7.4, containing 0.4M NaCl and 0.1% Triton X-100, and finally packed into a disposable plastic syringe to form a 5-ml column (hereinafter referred to as STI-Sepharose column).

EXAMPLE 2

Two liters of a culture supernatant of human melanoma cells (Bowes, ATCC CRL 1224 G361) containing 10% heat-inactivated (at 56° C. for 30 minutes) fetal calf serum and 20 KIU (kallikrein inhibitor units)/ml Aprotinin was stabilized with 0.02% Tween 80 (Wako Junyaku Co., Japan) and 0.4M NaCl and subjected to the STI-Sepharose column.

The effluent from the STI column was collected and the plasminogen-dependent fibrinolytic activity was measured. About 98% of the activity applied to the column was detected. The effluent was stabilized with 1.0M NaCl (final concentration) and then subjected to an ETI-Sepharose column. The effluent from the ETI column was collected and the plasminogen-dependent fibrinolytic activity was measured. About 10% of the activity applied to the column was detected. By zymography with an anti-human tPA antibody after SDS-polyacrylamide gel electrophoresis, the effluent exhibited two fractions for plasminogen activator, one with a molecular weight of $110,000 \pm 20,000$ daltons and the other with a molecular weight of 70,000 daltons. After running all the effluent through the column, the column was washed with a 20-fold column volume of a fluid containing 1.0M NaCl and 0.2% Tween 80. The fluid recovered had about 5% of the activity applied on the column and exhibited two plasminogen activator fractions by zymography, one with a molecular weight of $110,000 \pm 20,000$ daltons and the other with a molecular weight of 70,000 daltons.

Proteins adsorbed on the column were eluted applying a linear pH gradient from 5.5 to 3.0 using 0.2M citric acid buffers containing 0.15M NaCl.

By this elution, two activity peaks were observed, one peak eluted at the pH between 5.2 to 4.5 and the other at the pH between 4.5 to 3.7. These two fractions exhibited a common molecular weight of 70,000 daltons on SDS-polyacrylamide gel electrophoresis. The activity of these fractions combined was about 80–85% of the activity applied on the column.

These two fractions after the reduction with betamercaptoethanol were subjected to SDS-polyacrylamide gel electrophoresis, and then a silver staining analysis. It was revealed that the fraction eluted at the pH ranging from 5.2 to 4.5 exhibited a band with a molecular weight of 70,000 daltons or rather slower migrating band on the gel after the reduction, whereas the fraction eluted at the pH ranging from 4.5 to 3.7 exhibited a band with molecular weight of 30,000 to 40,000 daltons but the band with a molecular weight of 70,000 daltons disappeared after the reduction. From this result, the tPA eluted with the buffer at the pH between 5.2 to 4.5 was identified as sc-TPA and the tPA eluted at the pH between 4.5 to 3.7 was identified as dc-TPA.

EXAMPLE 3

Two litters of a culture supernatant of human fetal foreskin cells (Flow 7000 (Flow Laboratories Inc. USA)) containing 10% heat-inactivated (at 56° C. for 30 minutes) fetal calf serum and 20 KIU/ml Aprotinin was stabilized with 0.02% Tween 80 and 0.4M NaCl and subjected to a STI-Sepharose column in the same manner as described in Example 2.

The effluent from the STI column was collected and the plasminogen-dependent fibrinolytic activity was measured. About 98% of the activity applied to the column was detected. The effluent was stabilized with 1.0M NaCl (final concentration) and then subjected to an ETI-Sepharose column.

The effluent from the ETI column was collected and the plasminogen-dependent fibrinolytic activity was measured. About 45% of the activity applied to the column was detected. By zymography with an anti-human tPA antibody after SDS-polyacrylamide gel electrophoresis, the effluent exhibited several fractions, or bands, for plasminogen activator, a few bands approximate molecular weight of 100,000 daltons, several bands approximately 50,000 to 70,000 daltons and one band approximately 35,000 daltons.

The ETI-sepharose column was washed with a 20-fold column volume of 0.1M $NH_4HCO_3$, pH 7.5, containing 1.0M NaCl and 0.2% Tween 80. The fluid recovered had about 5% of the activity applied on the column and exhibited the same zymographic bands as described above.

Elution was carried out in the same manner as described in Example 2, except that buffers containing 0.15M NaCl and 0.1M glycine, pH 4.5 and pH 3.5, were applied.

As a result, an eluting pattern similar to that in Example 2 was observed. The activity of the fractions combined was about 40–50% of the activity applied on the column. These two fractions exhibited a common molecular weight of 70,000 daltons on SDS-polyacrylamide gel electrophoresis. These two fractions after the reduction with beta-mercaptoethanol were subjected to SDS-polyacrylamide gel electrophoresis, and then a silver staining analysis. It was revealed that fraction eluted with the pH 4.5 buffer had a molecular weight of 70,000 daltons and did not exhibit a change in molecular weight or rather slower migrating band on the gel after the reduction, whereas the fraction eluted with the pH 3.5 buffer exhibited a band for molecular weight of 30,000 to 40,000 daltons but no band corresponding to a band for the molecular weight of 70,000 daltons after the reduction. From this result, the tPA eluted at pH 4.5 was identified as sc-TPA and the tPA eluted at pH 3.5 was identified as dc-TPA.

EXAMPLE 4

Two liters of a culture supernatanat of mouse fibroblast cells transformed with human tPA gene (U.S. patent application Ser. No. 932,209 now abandoned in favor of U.S. Application Ser. No. 344,496), supplemented with 2% heat-inactivated (at 56° C. for 30 minutes) fetal calf serum and 20 KIU/ml Aprotinin, was stabilized with 0.02% Tween 80 and 0.4M NaCl and subjected to a STI-Sepharose column.

The effluent from the STI column as collected and the plasminogen-dependent fibrinolytic activity was measured. About 98% of the activity applied to the column was detected. The effluent was stabilized with 1.0M NaCl (final concentration) and then subjected to an ETI-Sepharose column.

The effluent from the ETI column was collected and the plasminogen-dependent fibrinolytic activity was measured. About 10% of the activity applied to the column was detected. By zymography with an anti-human tPA antibody after SDS-polyacrylamide gel electrophoresis, the effluent exhibited two fractions for plasminogen activator, one with a molecular weight of 110,000±20,000 daltons and the other with a molecular weight of 70,000 daltons. After running all the effluent through the column, the column was washed with a 20-fold column volume of a fluid containing 2.0M NaCl and 0.2% Tween 80. The fluid recovered had about 5% of the activity applied on the column and exhibited two plasminogen activator fractions by zymography, one with a molecular weight of 110,000±20,000 daltons and the other with a molecular weight of 70,000 daltons.

Proteins adsorbed on the column were eluted with 0.2M sodium phosphate solutions containing 0.15M NaCl, pH 4.5 and pH 3.5. The eluting pattern similar to that in Example 2 was obtained. The activity of the resultant two fractions combined was about 80% of the activity applied on the column. These two fractions exhibited a common molecular weight of 70,000 daltons on SDS-polyacrylamide gel electrophoresis.

These two fractions after the reduction with betamercaptoethanol were subjected to SDS-polyacrylamide gel electrophoresis, and then a silver staining analysis. It was revealed that the eluate with pH 4.5 solution exhibited a band with a molecular weight of 70,000 daltons and thus no change in molecular weight or rather slower migrating band on the gel after the reduction, whereas the eluate with pH 3.5 solution exhibited a band with a molecular weight of 30,000 to 40,000 daltons but no band corresponding to the band with a molecular weight of 70,000 daltons after the reduction. From this result, it was confirmed that the tPA eluted at pH 4.5 is sc-TPA and the tPA eluted at pH 3.5 was dc-TPA.

EXAMPLE 5

Two liters of a culture supernatant of human melanoma cells (Bowes, ATCC CRL 1224 G361) containing 10% heat-inactivated (at 56° C. for 30 minutes) fetal calf serum and 20 KIU/ml Aprotinin was stabilized with 0.02% Tween 80 and 1M NaCl and subjected to an ETI-Sepharose column.

The effluent from the column was collected and the plasminogen-dependent fibrinolytic activity was measured. About 10% of the activity applied to the column was detected. By zymography with an anti-human tPA antibody after SDS-polyacrylamide gel electrophoresis, the effluent exhibited two fractions for plasminogen activator, one having a molecular weight of 110,000±20,000 daltons and the other having a molecular weight of 70,000 daltons.

After running all the effluent through the column, the column was washed with a 20-fold column volume of a fluid containing 2M NaCl and 0.2% Tween 80. The fluid recovered had about 5% of the activity applied on the column and exhibited two plasminogen activator fractions by zymography, one with a molecular weight of 110,000±20,000 daltons and the other with a molecular weight of 70,000 daltons.

Proteins adsorbed on the column were eluted applying a linear pH gradient from 6.5 to 3.0 using 0.2M Veronal buffers containing 0.2M benzamidine and 0.15M NaCl.

By this elution, two activity peaks were observed, one peak eluted at the pH ranging from 6.0 to 4.5 and the other at the pH ranging from 4.5 to 3.5. These two fractions exhibited a common molecular weight of 70,000 daltons on SDS-polyacrylamide gel electrophoresis. The activity of these fractions combined was about 80–85% of the activity applied on the column.

These two fractions after the reduction with betamercaptoethanol were subjected to SDS-polyacrylamide gel electrophoresis, and then a silver staining analysis. It was revealed that the fraction eluted at the pH ranging from 6.0 to 4.5 exhibited a band with a molecular weight of 70,000 daltons and thus no change in the molecular weight or rather slower migrating band on the gel after the reduction, whereas the fraction eluted at the pH ranging from 4.5 to 3.5 exhibited a band with a molecular weight approximating to 30,000 to 40,000 daltons but the band with a molecular weight of 70,000 daltons disappeared after the reduction. From this result, the tPA eluted with the buffer at the pH between 6.0 to 4.5 was identified as sc-TPA and the tPA eluted at the pH between 4.5 to 3.5 was identified as dc-TPA.

EXAMPLE 6

Two liters of a culture supernatant of human fetal foreskin cells (Flow 7000) containing 10% heat-inactivated (at 56° C. for 30 minutes) fetal calf serum and 20 KIU/ml Aprotinin was stabilized with 0.02% Tween 80 and 1M NaCl and subjected to an ETI-Sepharose column.

The effluent from the ETI column was collected and the plasminogen-dependent fibrinolytic activity was measured. About 45% of the activity applied to the column was detected.

According to zymography with an anti-human tPA antibody after SDS-polyacrylamide gel electrophoresis, the effluent exhibited several fractions, or bands, for plasminogen activator, a few bands with molecular weights approximate 100,000 daltons, several bands with molecular weights approximately 50,000 to 70,000 daltons and one band with a molecular weight approximately 35,000 daltons.

The ETI-sepharose column was then washed with a 20-fold column volume of 0.1M disodium phosphate-sodium hydroxide buffer, pH 9.5, containing 2.0M NaCl. The fluid recovered had about 5% of the activity applied on the column and exhibited the same bands as described above by zymography.

Elution was carried out with 0.1M sodium phosphate-phosphoric acid solution containing 0.3M arginine and 0.15M NaCl (pH 5.5) and 0.2M citric acid buffer (pH 3.0) containing 0.15M NaCl.

As a result, two fractions were obtained from the eluate with buffers having different pHs. The activity of the fractions combined was about 40–50% of the activity applied on the column. These two fractions exhibited a common molecular weight of 70,000 daltons on SDS-polyacrylamide gel electrophoresis.

These fractions after the reduction with betamercaptoethanol were subjected to SDS-polyacrylamide gel electrophoresis, and then a silver staining analysis. It was revealed that the eluate with the pH 5.5 buffer exhibited a band with a molecular weight of 70,000 daltons and thus no change in molecular weight or rather slower migrating band on the gel after the reduction, whereas the eluate with the pH 3.0 buffer exhibited a band with a molecular weight of 30,000 to 40,000 daltons but the band corresponding to the band with a molecular weight of 70,000 daltons disappeared after the reduction.

From this result, the tPA eluted at pH 5.5 was identified as sc-TPA and the tPA eluted at pH 3.0 was identified as dc-TPA.

EXAMPLE 7

Two liters of a culture supernatant of mouse fibroblast cells transformed with human tPA gene (U.S. patent application Ser. No. 932,209 now abandoned in favor of U.S. Application Ser. No. 344,496), supplemented with 2% heat-inactivated (at 56° C. for 30 minutes) fetal calf serum and 20 KIU/ml Aprotinin, was stabilized with 1M NaCl and subjected to an ETI-Sepharose column.

The effluent from the ETI column was collected and the plasminogen-dependent fibrinolytic activity was measured. About 10% of the activity applied to the column was detected. By zymography with an anti-human tPA antibody after SDS-polyacrylamide gel electrophoresis, the effluent exhibited two fractions for plasminogen activator, one with a molecular weight of 110,000±20,000 daltons and the other with a molecular weight of about 70,000 daltons. After running all the effluent through the column, the column was washed with a 20-fold column volume of 2M NaCl solution. The fluid recovered had about 5% of the activity applied on the column and exhibited two bands for plasminogen activator by zymography, one with a molecular weight of 110,000±20,000 daltons and the other with a molecular weight of about 70,000 daltons.

Proteins adsorbed on the column were then eluted with 0.1M sodium phosphate buffer (pH 6.0) containing 0.5M benzamidine and 0.15M NaCl and 0.1M citric acid buffer (pH 3.0) containing 0.15M NaCl. Two different fractions were obtained in two different eluates. The activity of the resultant two fractions combined was about 80% of the activity applied on the column. These two fractions exhibited a common molecular weight of 70,000 daltons on SDS-polyacrylamide gel electrophoresis.

These two fractions after the reduction with betamercaptoethanol were subjected to SDS-polyacrylamide gel electrophoresis, and then a silver staining analysis. It was revealed that the eluate with pH 6.0 buffer exhibited a band with a molecular weight of about 70,000 daltons and thus no change in molecular weight or rather slower migrating band on the gel after the reduction, whereas the eluate with pH 3.0 buffer exhibited a band with a molecular weight of 30,000 to 40,000 daltons but no band corresponding to the molecular weight of about 70,000 daltons after the reduction. From this result, the tPA eluted at pH 6.0 was identified as sc-TPA and the tPA eluted at pH 3.0 was identified as dc-TPA.

EXAMPLE 8

Two liters of a culture supernatant of Chinese hamster ovary cells transformed with human tPA gene (CHO-cell C1271, ATCC CRL 1616) supplemented with 10% heat-inactivated (at 56° C. for 30 minutes) fetal calf serum and 40 KIU/ml Aprotinin was stabilized with 1M NaCl and subjected to a 5 ml volume of ETI-Sepharose column having been equilibrated with 0.5M sodium phosphate buffer (pH 7.5) containing 1.0M NaCl. The column was then washed with 0.05M Na$_2$HPO$_4$ (pH 9.5) containing 2.0M NaCl and 10 mM arginine.

The whole effluent from the ETI column had about 10% of the plasminogen-dependent fibrinolytic activity applied to the column and exhibited by zymography a band with a molecular weight of 110,000±20,000 daltons and a band with a molecular weight of about 70,000 daltons.

Proteins adsorbed on the column were first eluted with 0.05M Na$_2$HPO$_4$—NaOH buffer (pH 4.5) containing 0.01M arginine and 0.1M NaCl. The fibrinolytic activity of the eluate was about 60% of the activity applied on the column. Proteins remaining on the column were eluted with 0.1M citric acid buffer (pH 3.0) containing 0.1M NaCl. About 25% of the activity applied on the column was recovered. These two fractions exhibited a common molecular weight of 70,000 daltons on SDS-polyacrylamide gel electrophoresis.

The eluate fractions after the reduction with betamercaptoethanol were subjected to SDS-polyacrylamide gel electrophoresis, and then a silver staining analysis. It was revealed that the eluate with the pH 4.5 buffer exhibited a band with a molecular weight of about 70,000 daltons and thus no change in a molecular weight or rather slower migrating band on the gel after the reduction, whereas the eluate with the pH 3.0 buffer exhibited a band with a molecular weight of 30,000 to 40,000 daltons but the band with a molecular weight of about 70,000 daltons disappeared after the reduction. From this result, it was confirmed that the tPA eluted at pH 4.5 was sc-TPA and the tPA eluted at pH 3.0 was dc-TPA.

From experimental results, the relation between the pH and concentration of arginine for eluting sc-TPA was revealed as follows. At pH 4.5, 1 mM–50 mM; at pH 5.0, 0.03M or more; at pH 5.5, 0.10M or more; and at pH 6.0, 0.2M or more.

EXAMPLE 9

One mol NaCl (final concentration) was added to 2 litters of a culture supernatant of human fetal amniotic cells (FL, ATCC CCL-62) transformed with human tPA gene associated with human cytomegalovirus (HCMV) as a promoter for human tPA expression. The cell culture supernatant was then subjected to purification of single-chain tPA and double-chain tPA using an ETI column in the same manner as described in Example 8.

The fibrinolytic activity of the fractions eluted at 4.5 and at 3.0 was about 70% and about 15%, respectively, of that applied on the column.

EXAMPLE 10

Host cells, *Saccharomyces cerevisiae,* transformed with human tPA gene were cultured according to the conventional method (Principles and Practice of Recombinant DNA Research with Yeast in the Molecular Biology of Yeast Saccharomyces: Metabolism and Gene Expression, pp 603–636, Cold Spring Harbor Laboratory, Cold Spring Harbor, N.Y., 1982).

The cells were broken with glass beads and allowed to immerse in 0.05M sodium phosphate buffer (pH 7.5) containing 1M NaCl and 0.02% Tween 80 for extraction. The filtered extract was subjected to purification of tPA in the same manner as described in Example 6.

The eluate with the pH 5.5 buffer had a molecular weight of 70,000 daltons which was not changed by the reduction as carried out in the above examples 2–8, and exhibited the activity 85% of that applied on the column. The eluate with the pH 3.0 buffer changed its molecular weight (70,000 daltons) by the reduction, that is, a band with a molecular weight of 70,000 daltons disappeared and a band with a molecular weight of 30,000 to 40,000 daltons appeared, instead. About 10% of the activity applied to the column was observed in this eluate.

What is claimed is:

1. A method for separately purifying and separating single-chain tissue plasminogen activator (tPA) and double-chain tPA from a mixture containing both, which method comprises the steps of:
    (a) bringing a mixture containing single-chain tPAs and double chain tPAs into close contact with a column carrying an immobilized Erythrina trypsin inhibitor as an affinity agent to adsorb said tPAs onto said column;
    (b) treating said column with an eluent having a pH ranging from 4.5 to 6.0 to selectively elute single-chain tPA; and
    (c) treating said column with an eluent having a pH lower than 4.5 to selectively elute double-chain tPA.
2. A method as set forth in claim 1, in which said eluent contains an amidine derivative or a guanidine derivative.
3. A method as set forth in claim 2, in which said eluent contains an amidine derivative or a guanidine derivative at the concentration of at least 1 mM.
4. A method as set forth in claim 2, in which said amidine derivative is benzamidine.
5. A method as set forth in claim 2, in which said guanidine derivative is arginine.
6. A method as set forth in claim 1, in which said mixture is derived from a culture of tPA producing cells.
7. A method as set forth in claim 6, in which said cells are melanoma cells or human fetal foreskin cells.
8. A method as set forth in claim 6, in which said cells are recombinant cells transformed by introducing a human tPA gene.
9. A method as set forth in claim 8, in which said cells are Chinese hamster ovary cells, human fetal amniotic cells, yeast cells or mouse fibroblast cells.
10. A method for purifying and separating single-chain tPA from a mixture containing single-chain tPA and double-chain tPA, which comprises the steps of bringing said mixture into close contact with a column carrying an immobilized Erythrina trypsin inhibitor as an affinity agent to absorb said mixture of tPAs onto said column and then selectively eluting said single-chain tPA, having been adsorbed onto said column, with an eluent having a pH ranging from 4.5 to 6.0.
11. A method as set forth in claim 10, in which said eluent contains an amidine derivative or a guanidine derivative.
12. A method as set forth in claim 11, in which said eluent contains said amidine derivative or said guanidine derivative at the concentration of at least 1 mM.
13. A method as set forth in claim 11, in which said amidine derivative is benzamidine.
14. A method as set forth in claim 11, in which said guanidine derivative is arginine.
15. A method as set forth in claim 10, in which said mixture is derived from a culture of tPA producing cells.
16. A method as set forth in claim 15, in which said cells are melanoma cells or human fetal foreskin cells.
17. A method as set forth in claim 15, in which said cells are recombinant cells transformed by introducing a human tPA gene.
18. A method as set forth in claim 17, in which said cells are Chinese hamster ovary cells, human fetal amniotic cells, yeast cells or mouse fibroblast cells.

* * * * *